United States Patent [19]

Chapman et al.

[11] Patent Number: 5,821,346
[45] Date of Patent: Oct. 13, 1998

[54] METALLIZED CARBAMOYLAZO DYES

[75] Inventors: Derek D. Chapman, Rochester; Ramanuj Goswami, Webster; Csaba A. Kovacs, Rochester, all of N.Y.

[73] Assignee: Eastman Kodak Company, Rochester, N.Y.

[21] Appl. No.: 882,319

[22] Filed: Jun. 25, 1997

[51] Int. Cl.⁶ .............................. C07C 245/02; G03B 1/72
[52] U.S. Cl. ............................................. 534/560; 430/275
[58] Field of Search .............................. 534/560; 430/275

[56] References Cited

U.S. PATENT DOCUMENTS 5,426,015  6/1995  Chapman et al. ........................ 430/275
5,500,325  3/1996  Chapman et al. .................. 430/270.16

*Primary Examiner*—Zinna Northington Davis
*Attorney, Agent, or Firm*—John R. Everett

[57] ABSTRACT

Metallized carbamoylazo dyes having an azo group linking a substituted 3-hydroxypyridine nucleus to a phenyl nucleus are disclosed. The phenyl nucleus has a carbamoyl substituent ortho to the azo group. The dyes are useful in optical recording elements.

5 Claims, 1 Drawing Sheet

METALLIZED CARBAMOYLAZO DYES

FIELD OF THE INVENTION

The present invention relates to dyes and optical recording elements generally and DVD optical recording elements in particular.

BACKGROUND OF THE INVENTION

Optical recording elements for recording and storing digital information are known. One of the currently popular optical recording element is the compact disc or CD. CDs and recordable CDs (CD-Rs) have transformed the personal entertainment, personal computer and data storage industries. CDs and CD-Rs have made it possible to store enormous amounts of music or data on inexpensive, reliable, mass produced media.

Digital Versatile Disc (DVD) and recordable DVD (DVD-R) optical recording elements are being developed. For reasons stated below these elements have significantly greater storage capacity than CDs.

In CDs and DVDs digital information is stored in the form of low reflective marks on an otherwise reflective background. In this format the optical information is in the form of read only memory or ROM. Optical information is not recorded in real time, but is produced by press molding. In a typical process a substrate is stamped with a master containing the digital information in an embossed form. The stamped substrate, bearing deformations caused by the embossed master, is coated with a reflective layer and then with a protective layer. In the stamped substrate areas having the deformations the reflectivity is lower than in undeformed areas.

DVD elements have significantly more stringent requirements than CDs. The recording wavelength is 635 nm instead of 780 nm; playback wavelengths are 635 nm and 650 nm instead of 780 nm; numerical aperture of the read head is 0.6 instead of 0.5; the track pitch is 0.8 $\mu$m instead of 1.6 $\mu$m and the minimum mark length is 0.44 $\mu$m instead of 0.83 $\mu$m. These changes increase the data storage capacity significantly. In DVD the thickness of the stamped substrate is only 0.6 mm instead of 1.2 mm. However a total substrate thickness of 1.2 mm is required to make DVD elements physically stiffer and the same dimension as the popular CDs. This makes them useful in the current population of DVD modified CD players. Generally this is satisfied by forming a laminate structure that includes a substrate on opposite sides of other DVD required layers. Each substrate may be stamped with stored information. Or only one is so stamped.

It is sometimes desirable to produce an optical recording elements that can be recorded in real time. CD-R elements having this capability are known. Such elements have dye containing optical recording layers coated onto a grooved substrate. The recording layer is coated with a reflectivity layer and then a protective layer. Exposure of the element to a laser recording beam operating in the region of 780 nm forming a relatively low reflective mark.

U.S. Pat. No. 5,500,325 to Chapman et al discloses dye mixtures for optical recording layers. The mixtures comprise metallized azo ether dyes and a second dye. U.S. Pat. No. 5,426,015 discloses optical recording layers comprising metallized azo dianion with two cationic dye counterions.

DVD-R elements are constructed and used similarly to CD-R elements. However in DVD-R elements the shorter recording and playback wavelengths necessitates the development of new and different dye based optical recording layers.

SUMMARY OF THE INVENTION

The present invention provides a metallized carbamoylazo dye having an azo group linking a substituted 3-hydroxypyridine nucleus to a phenyl nucleus wherein the phenyl nucleus has a carbamoyl substituent ortho to the azo group.

The dyes have good recording sensitivity and excellent light and dark stability.

DETAILED DESCRIPTION OF THE INVENTION

Figure 1:
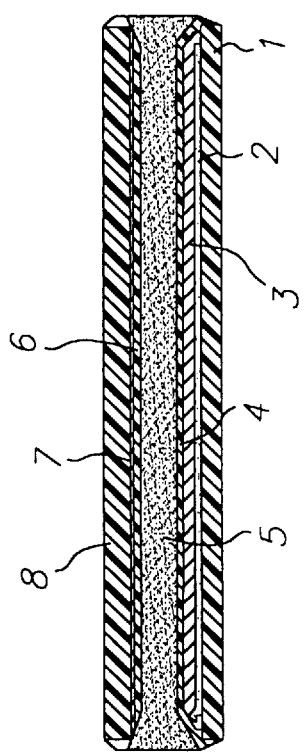
FIG. 1 presents a DVD optical recording element having a single optical recording layer.

Novel metallized carbamoylazo dyes included in this invention include those having the formula (I):

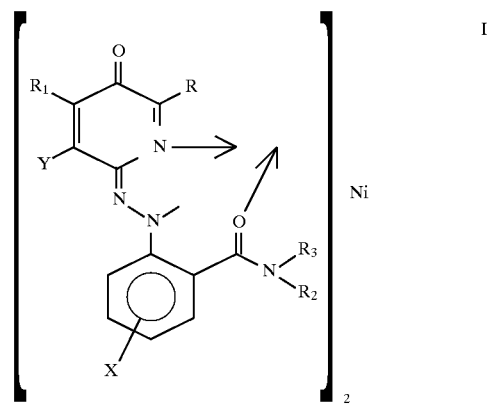

wherein;

R represents alkyl of 1 to about 10 carbons, amino, alkylamino of 1 to 10 carbons, dialkylamino of 1 to 10 carbons, or substituted or unsubstituted benzylamino, halogen or alkoxy of 1 to 10 carbons;

$R_1$ represents hydrogen or an alkyl of from 1 to 6 carbons;

Y represents hydrogen, an alkyl of from 1 to 6 carbons or alkoxy with 1 to 10 carbons or halogen;

X represents hydrogen, an alkyl of from 1 to 10 carbons or alkoxy with 1 to 10 carbons or halogen;

$R_2$ and $R_3$ represent hydrogen, an alkyl of from 1 to 10 carbons, a substituted or unsubstituted benzyl; an aryl of from 6 to about 10 carbons or a hetaryl of from 5 to about 10 carbons; or $R_2$ and $R_3$ may be taken together to form a ring with 5 to 10 carbons, a heterocyclic ring with oxygen, nitrogen or sulfur with 4 to 10 carbons.

General preparation of the dyes of this invention is illustrated by the following single step preparation of the nickel complex of 2-amino-3-hydroxy-6-(2-N,N dipropylcarbamoylphenylazo) pyridine (dye 2 of Table 1, infra).

Nickel acetate (12.4 g) was added to dimethylformamide (280 mL) followed by 2-amino-N,N-dipropylbenzamide (22 g) and 2-amino-3-hydroxypyridine (11 g). Acetic acid (280 mL) was added and the mixture was stirred for 40 minutes at room temperature. The temperature was then lowered to ca. 5° C. and a solution of sodium nitrite (7.2 g in 20 mL of water) was added slowly over a period of 15 minutes. After 2 hours, sodium acetate (55 g) was added and after stirring for 20 minutes the mixture was poured into ice water (3 L). The complex was filtered off and washed with water. The crude product was dissolved in boiling 2-butanone (1L) and filtered hot. The filtrate was concentrated to 400 mL and cooled. The product dye 2 was filtered off and dried at 50° C. in the vacuum oven. The yield was 20.5 g (52%). $\lambda$max=531 nm $\epsilon$=9.1×10$^4$.

The compounds can also be made by a two step procedure involving the isolation of the unmetallized dye followed by metallization using nickel acetate in the second step.

A portion of representative compounds within formula I are presented in Table 1.

The indices of some metallized carbamoylazo dyes of Table 1 are listed in Table 2 below.

TABLE 2

Indices of the metallized carbamoylazo dyes

| Azo Dye No. | Azo Dye No. | Ratio Dyes | Index (n/k) at 650 nm |
|---|---|---|---|
| 1 | | | 2.11/0.094 |
| 3 | | | 2.20/0.11 |
| 2 | | | 2.09/0.088 |
| 13 | | | 2.07/0.084 |
| 17 | | | 1.90/0.005 |
| 18 | | | 1.90/0.001 |
| 20 | | | 2.26/0.131 |
| 2 | 13 | 1/1 | 2.07/0.093 |

TABLE 1

Metallized Azo Dyes

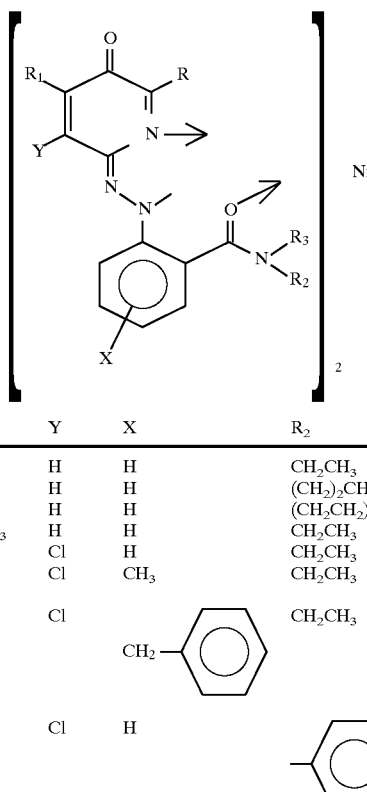

| Dye No | R | R$_1$ | Y | X | R$_2$ | R$_3$ |
|---|---|---|---|---|---|---|
| 1 | NH$_2$ | H | H | H | CH$_2$CH$_3$ | CH$_2$CH$_3$ |
| 2 | NH$_2$ | H | H | H | (CH$_2$)$_2$CH$_3$ | (CH$_2$)$_2$CH$_3$ |
| 3 | NH$_2$ | H | H | H | (CH$_2$CH$_2$)$_2$O | |
| 4 | NH$_2$ | CH$_3$ | H | H | CH$_2$CH$_3$ | CH$_2$CH$_3$ |
| 5 | NH$_2$ | H | Cl | H | CH$_2$CH$_3$ | (CH$_2$)$_2$CH$_3$ |
| 6 | NH$_2$ | H | Cl | CH$_3$ | CH$_2$CH$_3$ | (CH$_2$)$_2$CH$_3$ |
| 7 | NH$_2$ | H | Cl | CH$_2$—C$_6$H$_5$ | CH$_2$CH$_3$ | (CH$_2$)$_2$CH$_3$ |
| 8 | NH$_2$ | H | Cl | H | C$_6$H$_5$ | (CH$_2$)$_2$CH$_3$ |
| 9 | NH$_2$ | H | CH$_3$ | H | (CH$_2$)$_2$OCH$_3$ | (CH$_2$)$_2$CH$_3$ |
| 10 | NH$_2$ | CH$_3$ | H | H | (CH$_2$)$_2$OCH$_3$ | (CH$_2$)$_2$CH$_3$ |
| 11 | NH$_2$ | H | H | H | (CH$_2$CH$_2$)$_2$CH$_2$ | |
| 12 | NH$_2$ | CH$_3$ | H | H | (CH$_2$CH$_2$)$_2$CH$_2$ | |
| 13 | NH$_2$ | H | H | H | (CH$_2$)$_3$CH$_3$ | (CH$_2$)$_3$CH$_3$ |
| 14 | NH$_2$ | H | Cl | H | (CH$_2$)$_3$CH$_3$ | (CH$_2$)$_3$CH$_3$ |
| 15 | NH$_2$ | CH$_3$ | H | H | (CH$_2$)$_3$CH$_3$ | (CH$_2$)$_3$CH$_3$ |
| 16 | NH$_2$ | CH$_3$ | H | Cl | (CH$_2$)$_3$CH$_3$ | (CH$_2$)$_3$CH$_3$ |
| 17 | Cl | H | H | H | (CH$_2$)$_3$CH$_3$ | (CH$_2$)$_3$CH$_3$ |
| 18 | Br | H | H | H | (CH$_2$)$_3$CH$_3$ | (CH$_2$)$_3$CH$_3$ |
| 19 | CH$_3$ | H | H | H | (CH$_2$)$_3$CH$_3$ | (CH$_2$)$_3$CH$_3$ |
| 20 | NH$_2$ | H | H | H | (CH$_2$)$_3$CH$_3$ | H |

Optical Recording Elements

Broadly optical elements provided by the invention comprise a light transmitting, typically pregrooved substrate, a dye recording layer overlaying the substrate, a light reflective layer overlaying the light absorptive layer and a protective layer overlaying the light reflective layer. The recording process will produce marks of lower reflectivity than the unmarked areas of the disk when written and read with a diode laser emitting between 400 and 660 nm. The substituents on the dye molecules are selected such that the real part of the complex refractive index (n) of the unwritten recording layer measured with a light source having a selected wavelength from 400 to 660 nm is greater than 1.8 and the imaginary part (k) is less than 0.2.

Several different layer configuration embodiments are possible for DVD optical recording elements. Two embodiments are presented in FIGS. 1 and 2.

In the FIG. 1 embodiment the DVD element comprises the following layer arrangement:

(a) a transparent grooved substrate (1) having a groove width of from 100 to 800 nm; a groove depth of 30 to 270 nm; and a groove pitch of 0.5 to 1.8 μm, usually 0.8 μm or below.

(b) an optical recording layer (2) comprising a metallized carbamoylazo dye having an azo group linking a substituted 3-hydroxypyridine nucleus to a phenyl nucleus wherein the phenyl nucleus has a carbamoyl substituent ortho to the azo group wherein the recording layer. The unrecorded recording layer has a refractive index, at a selected wavelength from 645 to 655 nm, comprising a real part (n) greater than 1.8 and an imaginary part (k) less than 0.2.

(c) a light reflecting layer (3).

(d) a protective layer (4).

(e) an adhesive layer (5).

(f) a protective layer (6).

(g) a reflective layer (7).

(h) a substrate (8).

In the embodiment presented in FIG. 1 one or more of layers (d), (f) and (g) may be omitted.

Figure 2:
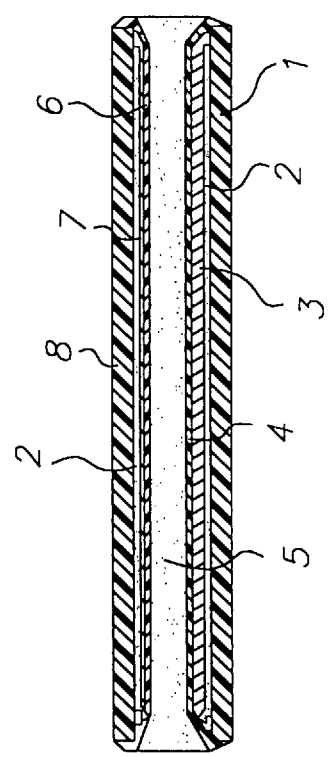
FIG. 2 presents a DVD optical recording element having two optical recording layers.

In the FIG. 2 embodiment the DVD element comprises the following layer arrangement:

(a) a transparent grooved substrate (1) having a groove width of from 100 to 800 nm; a groove depth of 30 to 270 nm; and a groove pitch of 0.5 to 1.8 μm, usually 0.8 μm or below.

(b) an optical recording layer (2) comprising a metallized carbamoylazo dye having an azo group linking a substituted 3-hydroxypyridine nucleus to a phenyl nucleus wherein the phenyl nucleus has a carbamoyl substituent ortho to the azo group the recording layer. The unrecorded recording layer has a refractive index, at a selected wavelength from 645 to 655 nm, comprising a real part (n) greater than 1.8 and an imaginary part (k) less than 0.2.

(c) a light reflecting layer (3).

(d) a protective layer (4).

(e) an adhesive layer (5).

(f) a protective layer (6).

(g) a reflective layer (7).

(h) an optical recording layer (2) comprising a metallized carbamoylazo dye having an azo group linking a substituted 3-hydroxypyridine nucleus to a phenyl nucleus wherein the phenyl nucleus has a carbamoyl substituent ortho to the azo group. The unrecorded recording layer has a refractive index, at a selected wavelength from 645 to 655 nm, comprising a real part (n) greater than 1.8 and an imaginary part (k) less than 0.2.

(i) a transparent grooved substrate (8) having a groove width of from 100 to 800 nm; a groove depth of 30 to 270 nm; and a groove pitch of 0.5 to 1.8 μm, usually 0.8 μm or below.

In some FIG. 2 embodiments one or both of the protective layers (d) and (f) may be omitted.

The substrate may be any transparent material that satisfies the mechanical and optical requirements. The substrates are generally pregrooved with groove depths from 20 nm to 250 nm, groove widths 0.2 to 1 mm and a pitch 0.5 to 2 mm particularly for CD-R. For DVD-R elements substrates the required groove specifications are mentioned in the description of FIGS. 1 and 2 above. The preferred material is polycarbonate, other materials are glass, polymethylmethacrylate and other suitable polymeric materials.

The preparation of the optical recording elements of the invention is achieved by spin coating of the dye mixture, with or without addenda, from a suitable solvent onto a transparent substrate. For coating, the dye mixture, with or without addenda, is dissolved in a suitable solvent such that the dye is 20 or less parts by weight to 100 parts of solvent by volume. The dye recording layer of the element is then overcoated with a metal reflective layer under reduced pressure by resistive heating or a sputter method and finally overcoated with a protective resin.

Coating solvents for the dye recording layer are selected to minimize their effect on the substrate. Useful solvents include alcohols, hydrocarbon halides, cellosolves, ketones. Examples of solvents are 2,2,3,3-tetrafluoropropanol, tetrachloroethane, dichloromethane, methyl cellosolve, ethyl cellosolve, 1-methoxy-2-propanol, 4-hydroxy-4-methyl-2-pentanone. Preferred solvents are alcohols since they have the least effect on the preferred polycarbonate substrates. Mixtures containing these solvents can also be used.

Useful addenda for the recording layer include stabilizers, surfactants, binders and diluents.

The reflective layer can be any of the metals conventionally used for optical recording materials. Useful metals can be vacuum evaporated or sputtered and include gold, silver, aluminum, copper and alloys thereof.

The protective layer over the reflective layer is similarly conventional for this art. Useful materials include UV curable acrylates.

An intermediate layer, to protect the metal layer from oxidation, can also be present.

In DVD elements the adhesives can be applied using screen printing, hot roller and spin coating methods. The adhesives to form the laminates include UV curable adhesives, hot melt adhesives, UV initiated cationic polymeric adhesives, pressure sensitive adhesives and acrylates.

The refractive index values for unrecorded recording layers was determined by coating a layer of the dye on a silicon wafer. The refractive index values (n and k) were measured by a Variable Angle Spectroscopic Ellipsometer (VASE) manufactured by J. A. Woollan Company.

The following examples demonstrate the recording sensitivity and light and dark stability of the optical recording layers provided by this invention.

For each of the dyes studied a complete DVD recording element according to FIG. 1 was prepared as presented in the examples.

EXAMPLE 1

In this example a DVD type optical recording element according to FIG. 1 was prepared and tested. A first assembly was prepared comprising, in the following order, substrate, recording layer, reflective layer and protective layer. The second assembly comprised, in the following order, a substrate, a reflecting layer and a protective layer.

This first assembly was then laminated with an adhesive to the second assembly, protective layer to protective layer. The dye for the recording layer was selected from Table 1.

First assembly

A polycarbonate substrate having a thickness of 0.6 mm, a diameter of 120 mm and a center hole diameter of 15 mm with a spiral groove on its surface with a width of 300 nm, a depth of 140 nm and a pitch of 0.8 mm, was made by injection molding.

To form the optical recording layer 1 part by weight of dye 2 was dissolved with ultrasound at room temperature in 1 hour in 50 parts of 2,2,3,3-tetrafluoropropanol by volume. The solution was filtered through a 0.2 µm filter. The solution was spin coated on the surface of the substrate to an overall optical density of 0.64 at 526 nm. The coating was dried at 60° C. for 30 minutes.

A gold reflective layer was deposited by a sputter process between 19.05 mm and 59.29 mm radii on the dye recording layer to about 40 nm thickness. For the deposition a Uniline 3000 made by First Light Technologies equipped with a Torus 10 DC magnetron source was used. Ionized argon gas was the gold carrier gas at 6000WS (+/−1000) deposition energy level.

A protective layer(DaiNippon Daicure SD-220) was spin coated over the gold reflective layer to a thickness of 7 to 11 mm. The protective layer was UV cured by the Fusion F300 series cure station with an 'H+' bulb in 2.6 seconds.

Second assembly

This assembly was prepared as in the first assembly using the substrate, reflective and protective layers.

The completed DVD element was prepared by laminating the first and second assemblies together through their respective protective layers. The laminate was formed by applying Sony SK7000 UV curable adhesive with an Autoroll 560 print head programmed for individual discs. The adhesive was silk-screened on to the protective layer of each assembly through a 305 mesh Kodak DOC (durable overcoat) silk-screen with a 90 durometer squeegee used at a 70 degree angle. Each assembly was UV cured at a rate of 10.668 meters per minute under a Fusion 450 UV lamp 25.4 cm "H" bulb. The two assemblies were mated adhesive to adhesive on a locating spindle and 35.6N (8 pound force) was applied for 2 minutes. The thus formed DVD element was allowed to remain a rest on the spindle for 5 minutes (which resulted in about 90% cure). To be fully cured before testing, the DVD element was left to stand for 24 hours.

To test the DVD element a test system consisting of an optical head with a 635 nm laser, a 0.6 NA lens, push-pull tracking, and ½ aperture focusing was used. The optics used circularly polarized light to reduce laser feedback effects. Recording and play back were carried out with the same laser at 3.84 m/s rotational speed. The read power was kept at 0.5 mW. Single frequency marks were recorded with a 1.61 µm mark length at 10 mW write power thereby forming marks of lower reflectivity than the unmarked area when examined with a light source emitting at 635 nm light. When the marks were read with the read laser, through a 30 Khz bandpass filter centered at the mark carrier frequency for this recording layer, a CNR (carrier to noise ratio) of 52 dB was obtained.

EXAMPLE 2

In this example the same disk substrate solvent, solution concentration, filter, spin coater, drying conditions, gold deposition process, lacquer layer application, lamination and testing procedure was used as in the first example. Dye 1 was coated on the grooved surface of the substrate to an overall optical density of 0.67 at 526 nm. When written with 8 mW write power a 55 dB CNR was obtained on reading.

EXAMPLE 3

In this example the same disk substrate solvent, solution concentration, filter, spin coater, drying conditions, gold deposition process, lacquer layer application, lamination and testing procedure was used as in the first example. Dye 3 was coated on the grooved surface of the substrate to an overall optical density of 0.62 at 526 nm. When written with 10 mW write power a 55 dB CNR was obtained on reading.

EXAMPLE 4

In this example the same disk substrate solvent, solution concentration, filter, spin coater, drying conditions, gold deposition process, lacquer layer application, lamination and testing procedure was used as in the first example. Dye 13 was coated on the grooved surface of the substrate to an overall optical density of 0.63 at 526 nm. When written with 10 mW write power a 50 dB CNR was obtained on reading

EXAMPLE 5

In this example the same disk substrate solvent, solution concentration, filter, spin coater, drying conditions, gold deposition process, lacquer layer application, lamination and testing procedure was used as in the first example. Dye 20 was coated on the grooved surface of the substrate to an overall optical density of 0.68 at 526 nm. When written with 9 mW write power a 59 dB CNR was obtained on reading.

EXAMPLE 6

In this example the same filter, spin coater, drying conditions, gold deposition process, protective layer application, lamination and testing procedure was used as in the first example. A mixture of 1 part dye 2 and 1 part of dye 13 was coated on the grooved surface of the substrate to an overall optical density of 0.46 at 526 nm. The coating solvent was a mixture of 77.6 parts of 1-methoxy-2-propanol and 2.4 parts of 4-hydroxy-4-methyl-2-pentanone. The substrate had a groove depth of 185 nm and a groove width of 281 nm. When written with 10 mW write power a 57 dB CNR was obtained on reading.

EXAMPLE 7

Light Stability

The selected dyes were spin coated on 5.08 by 5.08 cm (2 by 2 inch) polycarbonate slides. Optical density measurements were taken 5 mm from the edge of the slides with a Hewlett Packard 8450A Diode Array Spectrophotometer between 300 nm and 800 nm wave lengths. The slide was exposed through the polycarbonate for sixteen days by a method recommended by the Image Stability Technical Center for standard 50 klux Daylight exposure(ANSI IT9.9-1990 "Stability of Color Photographic Images" Section 5 Paragraph 5.6 Describes Simulated Indoor Indirect Daylight exposure). After sixteen days the optical densities were re-measured. To calculate the percent optical density loss, from the optical density value at λ-max before light exposure the optical density value after light exposure was subtracted. The resulting value was divided by the optical density value before light exposure and multiplied by one hundred. Results are presented in Table 3:

TABLE 3

| | Light Stability |
|---|---|
| Dye No. | % Optical Density Loss After 16 days 50 Klux Light Exposure |
| 1 | 3.9 |
| 2 | 4.0 |
| 3 | 3.8 |
| 13 | 3.3 |
| 2/13 (1:1 mixture) | 2.9 |

Table 3 shows the excellent light stability of the recording layers provided by the invention.

EXAMPLE 8

Dark Stability

The dyes were spin coated on 5.08 by 5.08 cm (2 by 2 inch) polycarbonate slides. Optical density measurements were taken before incubation with a Hewlett Packard 8450A Diode Array Spectrophotometer between 300 nm and 800 nm wave lengths. The slides were incubated for six weeks in a Hotpack Temperature Humidity Chamber (Model 434304) set at 80° C. temperature and 80% relative humidity with the slides placed, dye side up, in Petri dishes with the tops slightly open. Then optical measurements were taken after six weeks of incubation. To determine the percent optical density loss, from the optical density value at λ-max before incubation the optical density value after incubation was subtracted. The resulting number was divided by the optical density value before incubation and multiplied by one hundred to give the percent loss in optical density as a result of incubation. Results are presented in Table 4:

TABLE 4

Dark Stability

| Table 1 Dye No. | % Optical Density Loss After 6 weeks at 80° C./80% RH |
|---|---|
| 1 | 3.9 |
| 2 | 3.7 |
| 3 | 3.8 |

Table 4 shows the excellent dark stability of the optical recording layers provided by the invention.

The invention has been described in detail with particular reference to certain preferred embodiments thereof, but it will be understood that variations and modifications can be effected within the spirit and scope of the invention.

What is claimed is:

1. A metallized carbamoylazo dye having an azo group linking a substituted 3-hydroxypyridine nucleus to a phenyl nucleus wherein the phenyl nucleus has a carbamoyl substituent ortho to the azo group.

2. The dye of claim 1 having the formula (I):

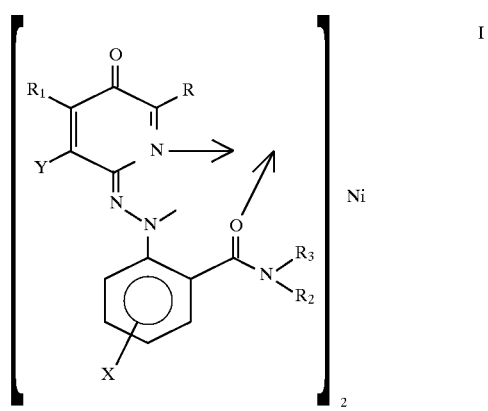

wherein;

R represents alkyl of 1 to about 10 carbons, amino, alkylamino of 1 to 10 carbons, dialkylamino of 1 to 10 carbons, or substituted or unsubstituted benzylamino, halogen or alkoxy of 1 to 10 carbons;

$R_1$ represents hydrogen or an alkyl of from 1 to 6 carbons;

Y represents hydrogen, an alkyl of from 1 to 6 carbons or alkoxy with 1 to 10 carbons or halogen;

X represents hydrogen, an alkyl of from 1 to 10 carbons or alkoxy with 1 to 10 carbons or halogen;

$R_2$ and $R_3$ represent hydrogen, an alkyl of from 1 to 10 carbons, a substituted or unsubstituted benzyl; an aryl of from 6 to about 10 carbons or a hetaryl of from 5 to about 10 carbons; or $R_2$ and $R_3$ may be taken together to form a ring with 5 to 10 carbons, a heterocyclic ring with oxygen, nitrogen or sulfur with 4 to 10 carbons.

3. The dye of claim 2 wherein R is amino.

4. The dye of claim 2 selected from Table 1 as follows:

TABLE 1

Metallized Azo Dyes

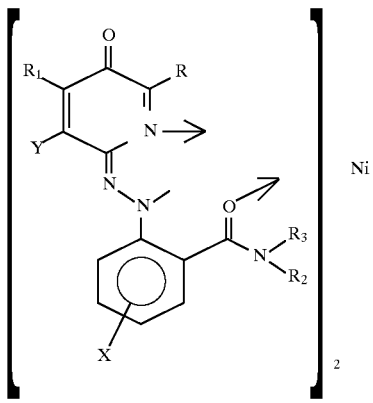

| Dye No | R | $R_1$ | Y | X | $R_2$ | $R_3$ |
|---|---|---|---|---|---|---|
| 1 | $NH_2$ | H | H | H | $CH_2CH_3$ | $CH_2CH_3$ |
| 2 | $NH_2$ | H | H | H | $(CH_2)_2CH_3$ | $(CH_2)_2CH_3$ |
| 3 | $NH_2$ | H | H | H | $(CH_2CH_2)_2O$ | |
| 4 | $NH_2$ | $CH_3$ | H | H | $CH_2CH_3$ | $CH_2CH_3$ |
| 5 | $NH_2$ | H | Cl | H | $CH_2CH_3$ | $(CH_2)_2CH_3$ |
| 6 | $NH_2$ | H | Cl | $CH_3$ | $CH_2CH_3$ | $(CH_2)_2CH_3$ |

TABLE 1-continued

Metallized Azo Dyes $$\left[ \begin{array}{c} \text{structure with } R_1, R, Y, X, R_2, R_3 \end{array} \right]_2 Ni$$

| Dye No | R | $R_1$ | Y | X | $R_2$ | $R_3$ |
|---|---|---|---|---|---|---|
| 7 | $NH_2$ | H | Cl | $CH_2$—C$_6$H$_5$ | $CH_2CH_3$ | $(CH_2)_2CH_3$ |
| 8 | $NH_2$ | H | Cl | H | C$_6$H$_5$ | $(CH_2)_2CH_3$ |
| 9 | $NH_2$ | H | $CH_3$ | H | $(CH_2)_2OCH_3$ | $(CH_2)_2CH_3$ |
| 10 | $NH_2$ | $CH_3$ | H | H | $(CH_2)_2OCH_3$ | $(CH_2)_2CH_3$ |
| 11 | $NH_2$ | H | H | H | $(CH_2CH_2)_2CH_2$ | |
| 12 | $NH_2$ | $CH_3$ | H | H | $(CH_2CH_2)_2CH_2$ | |
| 13 | $NH_2$ | H | H | H | $(CH_2)_3CH_3$ | $(CH_2)_3CH_3$ |
| 14 | $NH_2$ | H | Cl | H | $(CH_2)_3CH_3$ | $(CH_2)_3CH_3$ |
| 15 | $NH_2$ | $CH_3$ | H | H | $(CH_2)_3CH_3$ | $(CH_2)_3CH_3$ |
| 16 | $NH_2$ | $CH_3$ | H | Cl | $(CH_2)_3CH_3$ | $(CH_2)_3CH_3$ |
| 17 | Cl | H | H | H | $(CH_2)_3CH_3$ | $(CH_2)_3CH_3$ |
| 18 | Br | H | H | H | $(CH_2)_3CH_3$ | $(CH_2)_3CH_3$ |
| 19 | $CH_3$ | H | H | H | $(CH_2)_3CH_3$ | $(CH_2)_3CH_3$ |
| 20 | $NH_2$ | H | H | H | $(CH_2)_3CH_3$ | H. |

5. The dye of claim 4 selected from dyes 1, 2, 3, 13 and 20 of Table 1.

* * * * *